US011234808B2

(12) United States Patent
Govari et al.

(10) Patent No.: US 11,234,808 B2
(45) Date of Patent: Feb. 1, 2022

(54) PRESSURE CHANGER FOR A BREAST IMPLANT

(71) Applicant: BIOSENSE WEBSTER (ISRAEL) LTD., Yokneam (IL)

(72) Inventors: Assaf Govari, Haifa (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 184 days.

(21) Appl. No.: 16/781,170

(22) Filed: Feb. 4, 2020

(65) Prior Publication Data

US 2020/0170784 A1 Jun. 4, 2020

Related U.S. Application Data

(62) Division of application No. 15/432,585, filed on Feb. 14, 2017, now Pat. No. 10,548,712.
(Continued)

(51) Int. Cl.
*A61F 2/12* (2006.01)
*A61M 5/142* (2006.01)
(Continued)

(52) U.S. Cl.
CPC .............. *A61F 2/12* (2013.01); *A61M 5/142* (2013.01); *A61M 5/16804* (2013.01);
(Continued)

(58) Field of Classification Search
CPC .......... A61F 2/12; A61M 5/168; A61M 5/142
(Continued)

(56) References Cited

U.S. PATENT DOCUMENTS

| 146,805 A | 1/1874 | Cox |
| 1,091,063 A | 3/1914 | Hutchinson |

(Continued)

FOREIGN PATENT DOCUMENTS

| CN | 101284639 A | 10/2008 |
| DE | 19923183 A1 | 11/2000 |

(Continued)

OTHER PUBLICATIONS

Extended European Search Report for European Application No. 17158382.6-1664, dated Jul. 27, 2017, 8 pages.
(Continued)

*Primary Examiner* — Suzette J Gherbi
(74) *Attorney, Agent, or Firm* — Etan S. Chatlynne; Roberts Calderon Safran & Cole P.C.

(57) ABSTRACT

Apparatus, including an enclosure, a fluid-tight bag located within the enclosure, and a fluid-tight valve connected to the fluid-tight bag. The apparatus also has a tube, having a first end connected to the fluid-tight bag via the fluid-tight valve, and a second end connected to a balloon within a breast implant fitted to an implantee. The apparatus further includes a spindle, located within the enclosure, connected to the fluid-tight bag, and configured to rotate under control of the implantee so as to roll the fluid-tight bag onto the spindle or to unroll the fluid-tight bag from the spindle, and thus transfer a fluid, contained in the balloon, the tube, and the fluid-tight bag, therebetween.

10 Claims, 4 Drawing Sheets

Related U.S. Application Data

(60) Provisional application No. 62/301,180, filed on Feb. 29, 2016.

(51) Int. Cl.
*A61M 5/168* (2006.01)
*A61F 2/48* (2006.01)

(52) U.S. Cl.
CPC ....... *A61F 2/484* (2021.08); *A61F 2250/0003* (2013.01); *A61F 2250/0004* (2013.01)

(58) Field of Classification Search
USPC .......................................................... 623/7–8
See application file for complete search history.

(56) References Cited

U.S. PATENT DOCUMENTS

| | | |
|---|---|---|
| 1,263,798 A | 4/1918 | Otto |
| 3,852,833 A | 12/1974 | Koneke et al. |
| 3,919,724 A | 11/1975 | Sanders et al. |
| 3,934,274 A | 1/1976 | Hartley, Jr. |
| 4,433,440 A | 2/1984 | Cohen |
| 4,615,704 A | 10/1986 | Frisch |
| 4,624,671 A | 11/1986 | Kress |
| 4,643,733 A | 2/1987 | Becker |
| 4,773,908 A | 9/1988 | Becker |
| 4,775,379 A | 10/1988 | Fogarty et al. |
| 4,790,309 A | 12/1988 | Becker |
| 4,944,749 A | 7/1990 | Becker |
| 4,969,892 A | 11/1990 | Burton et al. |
| 4,969,898 A | 11/1990 | Calogero |
| 4,969,899 A | 11/1990 | Cox, Jr. |
| 5,019,101 A | 5/1991 | Purkait et al. |
| 5,181,907 A | 1/1993 | Becker |
| 5,219,360 A | 6/1993 | Georgiade |
| 5,507,808 A | 4/1996 | Becker |
| 5,549,672 A | 8/1996 | Maddock et al. |
| 5,630,843 A | 5/1997 | Rosenberg |
| 5,723,006 A | 3/1998 | Ledergerber |
| 5,776,159 A | 7/1998 | Young |
| 5,845,813 A * | 12/1998 | Werner ................ B65D 35/285 222/101 |
| 5,882,353 A * | 3/1999 | VanBeek ................ A61B 90/02 623/8 |
| 6,113,569 A | 9/2000 | Becker |
| 6,183,514 B1 | 2/2001 | Becker |
| 6,540,702 B1 | 4/2003 | Sarango |
| 6,755,861 B2 | 6/2004 | Nakao |
| 7,081,136 B1 | 7/2006 | Becker |
| 7,615,074 B2 | 11/2009 | Carvalio |
| 7,762,982 B1 | 7/2010 | Shah |
| 8,080,057 B2 | 12/2011 | Kronowitz |
| 8,197,542 B2 | 6/2012 | Becker |
| 8,202,317 B2 | 6/2012 | Becker |
| 8,308,630 B2 | 11/2012 | Birk et al. |
| 8,394,118 B2 | 3/2013 | Jones et al. |
| 8,398,710 B2 | 3/2013 | Forsell |
| 9,265,921 B2 | 2/2016 | Korman |
| 10,548,712 B2 * | 2/2020 | Govari .............. A61M 5/16804 |
| 2002/0011497 A1 | 1/2002 | Farris |
| 2005/0284215 A1 | 12/2005 | Falsetti |
| 2006/0069403 A1 | 3/2006 | Shalon et al. |
| 2006/0100578 A1 | 5/2006 | Liberman |
| 2006/0161196 A1* | 7/2006 | Widgerow ............ A61B 90/02 606/192 |
| 2007/0050026 A1 | 3/2007 | Carvalio |
| 2007/0276478 A1 | 11/2007 | Marmureanu et al. |
| 2008/0275569 A1 | 11/2008 | Lesh |
| 2009/0210056 A1 | 8/2009 | Forsell |
| 2010/0010531 A1 | 1/2010 | Shalon et al. |
| 2010/0010871 A1 | 1/2010 | Mengerink |
| 2010/0087843 A1 | 4/2010 | Bertolote et al. |
| 2010/0108717 A1* | 5/2010 | Szymanski ............ B65D 35/34 222/100 |
| 2010/0204792 A1 | 8/2010 | Greco |
| 2010/0211166 A1 | 8/2010 | Miller et al. |
| 2010/0228347 A1 | 9/2010 | Schuessler |
| 2010/0324688 A1 | 12/2010 | Doty |
| 2011/0106249 A1 | 5/2011 | Becker |
| 2011/0153017 A1 | 6/2011 | McClellan |
| 2011/0160854 A1 | 6/2011 | Berg et al. |
| 2011/0160859 A1 | 6/2011 | Doty |
| 2011/0230845 A1 | 9/2011 | Pascal et al. |
| 2011/0264213 A1 | 10/2011 | Demiranda |
| 2012/0059349 A1* | 3/2012 | Kuo ...................... A61J 1/067 604/500 |
| 2012/0116509 A1 | 5/2012 | Forsell |
| 2013/0007980 A1 | 1/2013 | Worker et al. |
| 2013/0013063 A1 | 1/2013 | Del Vecchio |
| 2013/0013084 A1 | 1/2013 | Birk |
| 2013/0079807 A1 | 3/2013 | Korman |
| 2013/0237915 A1 | 9/2013 | Barrelli et al. |
| 2013/0245758 A1 | 9/2013 | Chitre et al. |
| 2013/0341353 A1 | 12/2013 | Harris |
| 2014/0031619 A1 | 1/2014 | Moon |
| 2014/0100656 A1 | 4/2014 | Namnoum et al. |
| 2014/0142556 A1* | 5/2014 | Kuo .................. A61M 5/14276 604/891.1 |
| 2014/0156001 A1 | 6/2014 | Davodian |
| 2014/0200396 A1 | 7/2014 | Lashinski et al. |
| 2014/0221732 A1* | 8/2014 | Dayton .................. A61B 17/70 600/30 |
| 2014/0222145 A1* | 8/2014 | Kronowitz ................ A61F 2/12 623/8 |
| 2014/0236210 A1 | 8/2014 | Payne et al. |
| 2015/0038976 A1 | 2/2015 | Roschak et al. |
| 2015/0374906 A1* | 12/2015 | Forsell ...................... A61F 2/28 600/31 |
| 2016/0045312 A1 | 2/2016 | Braido et al. |
| 2016/0228603 A1 | 8/2016 | Nguyen et al. |
| 2016/0250017 A1 | 9/2016 | McClellan |
| 2016/0310711 A1 | 10/2016 | Luxon et al. |
| 2017/0079737 A1 | 3/2017 | Jones et al. |
| 2017/0127929 A1 | 5/2017 | Schutt et al. |
| 2017/0165025 A1 | 6/2017 | Payne et al. |
| 2017/0333179 A1 | 11/2017 | Forsell |
| 2018/0153684 A1 | 6/2018 | Van Heugten et al. |
| 2018/0200714 A1 | 7/2018 | Viovy et al. |
| 2018/0279889 A1 | 10/2018 | Lee |
| 2019/0091001 A1 | 3/2019 | Forsell |
| 2019/0111206 A1* | 4/2019 | Forsell ................ F04C 15/0061 |
| 2019/0223971 A1 | 7/2019 | Payne et al. |

FOREIGN PATENT DOCUMENTS

| | | |
|---|---|---|
| EP | 1547549 A2 | 6/2005 |
| EP | 2453839 B1 | 3/2014 |
| WO | 9504561 A1 | 2/1995 |
| WO | 2016003718 A1 | 1/2016 |

OTHER PUBLICATIONS

International Search Report and Written Opinion for International Application No. PCT/IB2018/056354, dated Nov. 16, 2018, 12 pages.
Mentor, "Becker Expander/Mammary Prostheses (Reconstruction Adjunct Study)," 2002, Retrieved from the internet http://www.mentorwwllc.com/documents/Becker.pdf, 16 pages.

* cited by examiner

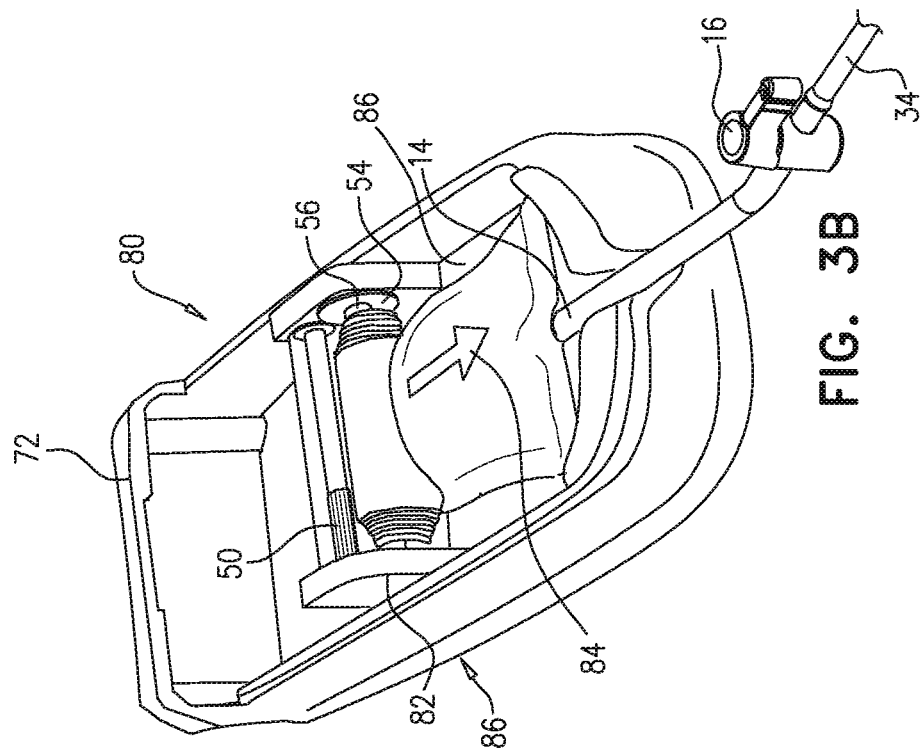
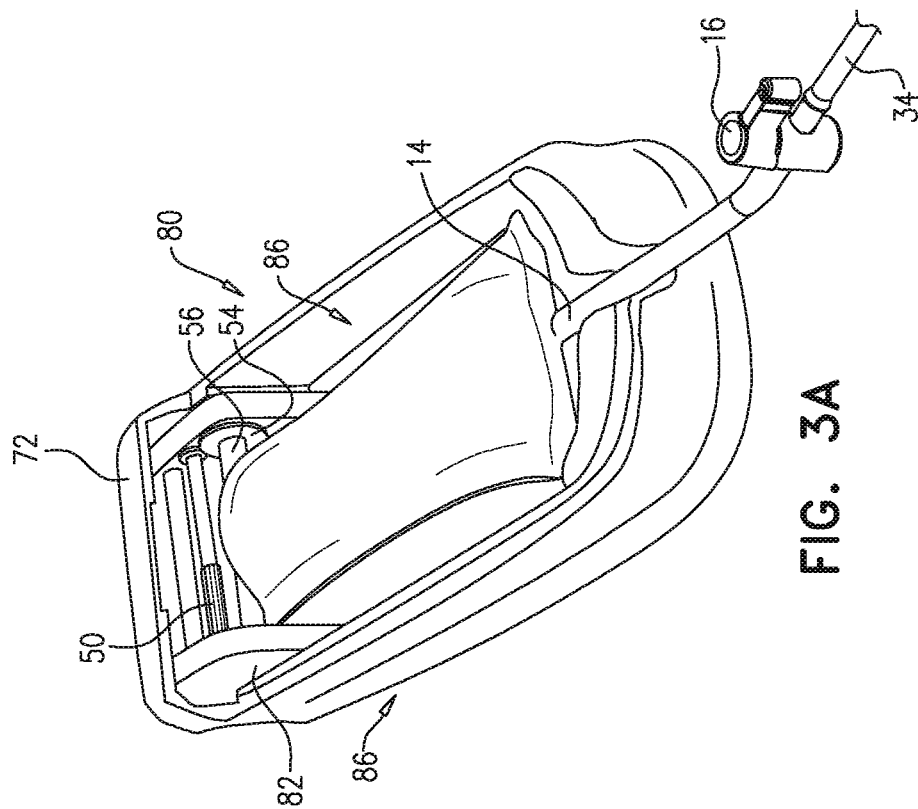
FIG. 3B
FIG. 3A

PRESSURE CHANGER FOR A BREAST IMPLANT

CROSS-REFERENCE TO RELATED APPLICATIONS

The present application is a Divisional Application under 35 U.S.C. § 121 of U.S. patent application Ser. No. 15/432,585, filed Feb. 14, 2017, which claims priority under 35 U.S.C § 119 to Provisional Patent Application No. 62/301,180, filed Feb. 29, 2016. The entire contents of these applications are incorporated by reference herein in their entirety

FIELD OF THE INVENTION

This invention relates generally to mastectomy, and specifically to procedures performed after a mastectomy.

BACKGROUND OF THE INVENTION

There are a number of devices which are known in the art that may be used after a mastectomy.

U.S. Pat. No. 3,852,833, to Koneke, et al., whose disclosure is incorporated herein by reference, describes a breast prosthesis which comprises a semi-rigid flat bottom portion with a first inner covering portion extending over the bottom.

U.S. Pat. No. 4,433,440, to Cohen, whose disclosure is incorporated herein by reference, describes a breast prosthesis comprising inner and outer flexible containers, each having a self-sealing valve associated therewith. The valves are arranged in such a fashion that each container can be separately filled with fluid.

U.S. Pat. No. 8,080,057, to Kronowitz, whose disclosure is incorporated herein by reference, describes a prosthesis that may be inserted into a breast and may be inflated to preserve the shape of the breast skin envelope. The prosthesis may include a base, and a balloon coupled to the base, where the balloon may be inflated to preserve the shape of the breast skin envelope.

U.S. Pat. No. 8,394,118, to Jones, et al., whose disclosure is incorporated herein by reference, describes a tissue expansion system, comprising an implantable tissue expander comprising an expandable chamber completely surrounding a compressed gas reservoir, wherein the expandable chamber is adapted to be a non-elastic chamber with a pre-formed breast shape.

U.S. Patent Application 2005/0284215, to Falsetti, whose disclosure is incorporated herein by reference, describes apparatus for the preoperative estimation of breast implant volume, in which a volume of air, water, or other substance is used to inflate one or more bladders located within the cups of a brassiere-like garment.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:
an enclosure;
a fluid-tight bag located within the enclosure;
a fluid-tight valve connected to the fluid-tight bag;
a tube, having a first end connected to the fluid-tight bag via the fluid-tight valve, and a second end connected to a balloon within a breast implant fitted to an implantee; and
a spindle, located within the enclosure, connected to the fluid-tight bag, and configured to rotate under control of the implantee so as to roll the fluid-tight bag onto the spindle or to unroll the fluid-tight bag from the spindle, and thus transfer a fluid, contained in the balloon, the tube, and the fluid-tight bag, therebetween.

In a disclosed embodiment the apparatus includes a motor within the enclosure, connected to the spindle so as to rotate the spindle. The motor and the spindle may be configured to remain in a fixed position within the enclosure while the spindle rotates. Alternatively, the apparatus includes tracks within the enclosure along which the motor and the spindle are configured to slide while the spindle rotates.

In a further disclosed embodiment the apparatus includes a pressure sensor connected to the fluid-tight bag so as to measure pressure therein.

In a yet further disclosed embodiment the apparatus includes a controller within the enclosure configured to operate the spindle, and a further controller, located remote from the enclosure and under control of the implantee, configured to communicate wirelessly with the controller.

In an alternative embodiment the fluid consists of a liquid. Alternatively, the fluid consists of a gas.

There is further provided, according to an embodiment of the present invention, a method, including:
providing an enclosure;
locating a fluid-tight bag within the enclosure;
connecting a fluid-tight valve to the fluid-tight bag;
connecting a first end of a tube to the fluid-tight bag via the fluid-tight valve, and a connecting a second end of the tube to a balloon within a breast implant fitted to an implantee;
and
connecting a spindle, located within the enclosure, to the fluid-tight bag, and configuring the spindle to rotate under control of the implantee so as to roll the fluid-tight bag onto the spindle or to unroll the fluid-tight bag from the spindle, and thus transfer a fluid, contained in the balloon, the tube, and the fluid-tight bag, therebetween.

The present disclosure will be more fully understood from the following detailed description of the embodiments thereof, taken together with the drawings, in which:

BRIEF DESCRIPTION OF THE DRAWINGS

FIGS. 3A and 3B are schematic diagrams of an assembly base and operative elements of an assembly, according to an alternative embodiment of the present invention.

DETAILED DESCRIPTION OF EMBODIMENTS

Overview

After a mastectomy, a temporary implant, used to create a pocket, may be inserted into the breast. To create the pocket, a balloon, with a valve external to the breast, may be incorporated into the temporary implant and volumes of saline solution, each volume typically being of the order of 100 ml, may be periodically injected into the balloon. The time between injections is usually of the order of two—three weeks, and each injection typically requires a visit to a doctor's surgery. In addition, the relatively sudden injection of a large amount of fluid may be uncomfortable or even somewhat painful.

To overcome these problems, an embodiment of the present invention provides an enclosure, and a fluid-tight bag is located within the enclosure. A first end of a tube is connected to the fluid-tight bag via a fluid-tight valve that is connected to the bag. A second end of the tube is connected, typically via another fluid-tight valve, to a balloon within a breast implant fitted to an implantee.

A spindle is located within the enclosure and is connected to the fluid-tight bag. The spindle is under control of the implantee, and is configured to rotate the fluid-tight bag onto the spindle, or to unroll the fluid-tight bag from the spindle. The rolling and unrolling transfers fluid that is contained in the balloon, the tube, and the fluid-tight bag between these three elements.

Since the rolling and unrolling are under control of the implantee, the implantee is able to select the times of fluid injection to the balloon (or fluid removal from the balloon) to suit her schedule. Furthermore, it has been found that using an embodiment of the present invention is more comfortable than the periodic injections described above.

DETAILED DESCRIPTION

Figure 1:
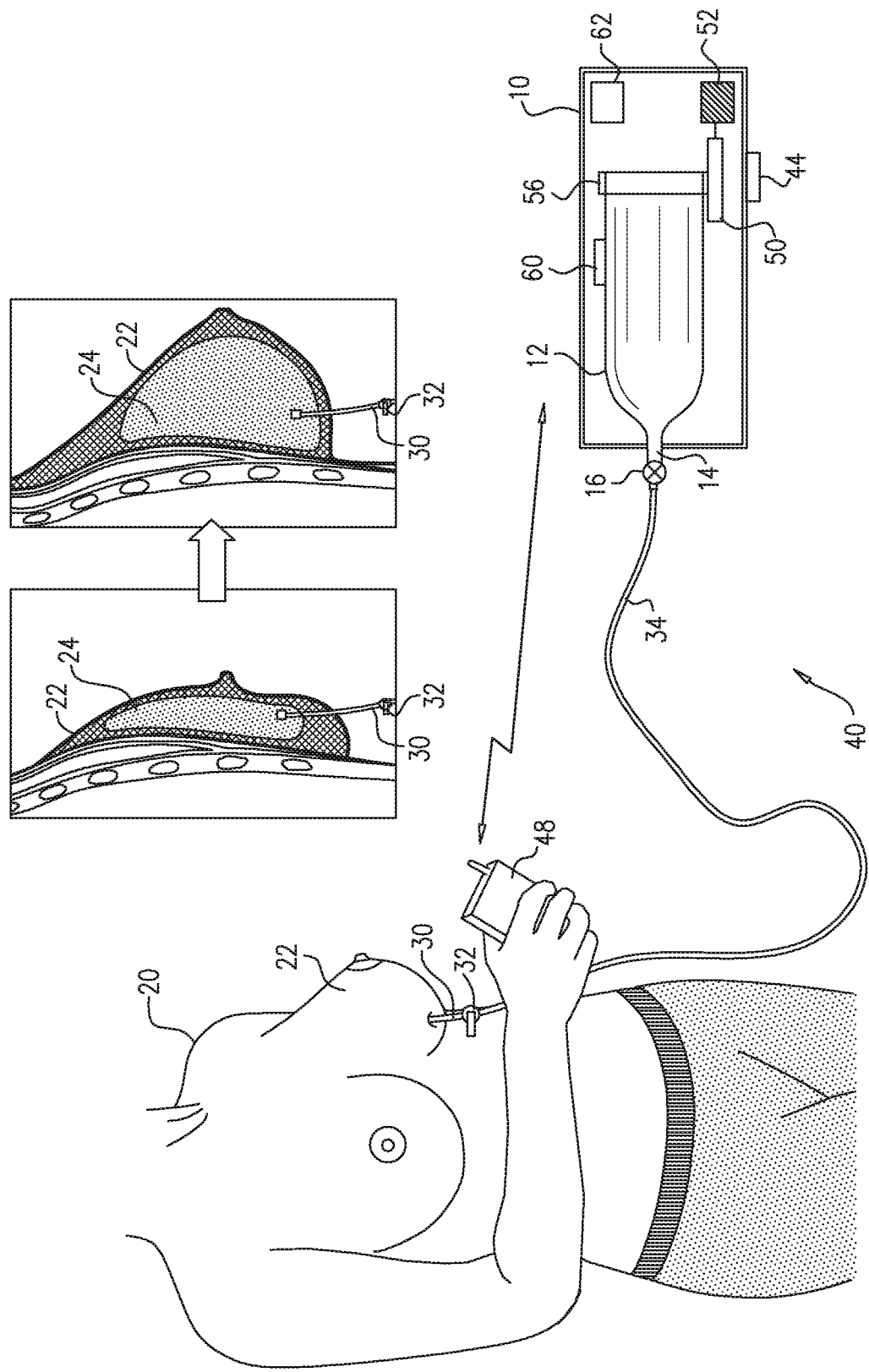
FIG. 1 is a schematic diagram illustrating use of a breast implant pressure changer assembly, according to an embodiment of the present invention.

Reference is now made to FIG. 1, which is a schematic diagram illustrating use of a breast implant pressure changer assembly 10, according to an embodiment of the present invention. Assembly 10 comprises within the assembly a fluid-filled, fluid-tight, bag 12, and the bag is coupled to a tube 14 that is terminated by a fluid-tight valve 16. Typically the fluid filling the bag comprises saline solution, although in some embodiments the fluid may comprise air. A user 20, also herein termed implantee 20, of assembly 10 has been fitted with a temporary implant 24 after a mastectomy on a breast 22. The implant comprises a balloon, so is also herein referred to as balloon 24. Balloon 24 is coupled to a tube 30 which is terminated by a fluid-tight valve 32. Valve 32 and at least part of tube 30 are external to breast 22, and so are typically designed to be relatively inconspicuous.

A coupling tube 34 connects between valve 16 and valve 32. When both valves are open, balloon 24, tubes 30, 34, and 14, and bag 12 form a closed sealed system 40. As described in more detail below user 20 is able to change the volume of bag 12, the change of volume leading to a change of pressure in system 40. The change of pressure in system 40 forms a corresponding change in pressure of balloon 24, leading in turn to a change of volume of the balloon. The change of volume of bag 12 typically comprises the user reducing the bag volume, leading to an increase in volume of the balloon. In some cases user 20 may desire to increase the bag 12 volume, for example to counteract an overpressure. Assembly 10 is consequently configured to allow the user to decrease or increase the volume of bag 12.

In some embodiments assembly 10 comprises a switch 44 which implantee 20 uses to change the volume of bag 12, i.e., to increase the volume of the bag or to decrease the volume of the bag. Alternatively or additionally, implantee 20 may change the volume of bag 12 using a remote system, for example by operating an application in a system controller 48, typically a smartphone, which communicates wirelessly with assembly 10. The wireless communication typically uses a standard protocol and technology, such as Bluetooth low energy (BLE).

A DC motor 50 is coupled to a spindle 56 around which bag 12 rolls or unrolls when the motor is operated. Motor 50 is powered by a battery 52, and the motor and the battery are both within assembly 10. A pressure sensor 60 is connected to bag 12, so as to measure the pressure of the fluid in the bag. Assembly 10 also comprises an assembly controller 62 which communicates with the pressure sensor and the DC motor so as to control the operation of rolling or unrolling of the bag. If, as explained above, a wireless remote system operates assembly 10, assembly controller 62 is also configured to communicate wirelessly with controller 48.

Figure 2:
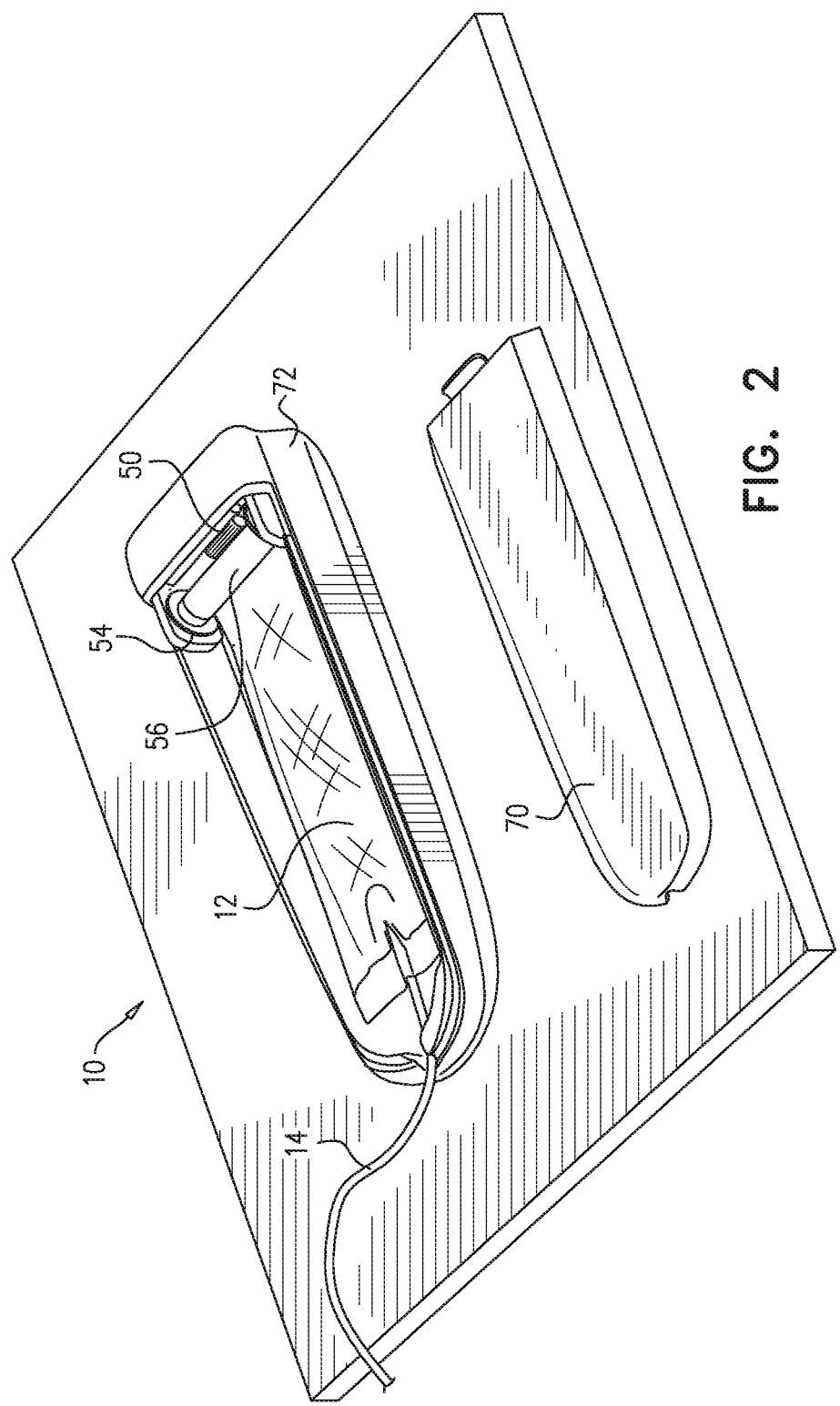
FIG. 2 is a schematic diagram of the assembly in a partly disassembled form, according to an embodiment of the present invention.

FIG. 2 is a schematic diagram of assembly 10 in a partly disassembled form, according to an embodiment of the present invention. Assembly 10 comprises a cover 70 which fits over an assembly base 72, the base holding operative elements of the assembly. Illustrated in FIG. 2 is bag 12, which connects to tube 14. When DC motor 50 is activated, it turns spindle 56, via gear wheels 54, so that the bag rolls or unrolls on the spindle. Motor 50, gear wheels 54, and spindle 56 are fixed within base 72. The figure illustrates assembly 10 with bag 12 in an unrolled configuration. When the bag rolls onto the spindle, it withdraws tube 14 into the assembly. When the bag unrolls from the spindle, the pressure in the bag, which is typically greater than atmospheric pressure, keeps the bag inflated and constrains the bag to move within assembly 10 so that tube 14 moves out from the assembly. (Connecting valve 16 is not illustrated in FIG. 2.) Mounted within assembly base 72, but not visible in the figure, are battery 52 and processor 62. Attached to bag 12, also not visible in the figure, is pressure sensor 60.

FIGS. 3A and 3B are schematic diagrams of assembly base 72 and operative elements of an assembly 80, according to an alternative embodiment of the present invention. Apart from the differences described below, the operation of assembly 80 is generally similar to that of assembly 10 (FIGS. 1 and 2), and elements indicated by the same reference numerals in both assembly 10 and assembly 80 are generally similar in construction and in operation. For simplicity, cover 70 is not shown in FIGS. 3A and 3B.

In contrast to assembly 10, in assembly 80 motor 50, gear wheels 54, and spindle 56 are mounted into a sub-assembly 82 which is constrained to move as a single unit within base 72, typically by providing tracks 86 along which the sub-assembly slides. FIG. 3A illustrates bag 12 when it is not rolled onto spindle 56. FIG. 3B illustrates bag 12 when it is partly rolled onto spindle 56. As for assembly 10, in assembly 80 the rolling or unrolling of the bag is controlled by rotation of motor 50. However, since sub-assembly 82 is able to move, rolling of the bag moves the sub-assembly in a direction shown by an arrow 84 in FIG. 3B. Unrolling of the bag moves the sub-assembly in a direction opposite to that of the arrow. The motion of the sub-assembly in the direction opposite to that of the arrow is assisted by the pressure of the fluid in bag 12. In contrast to assembly 10, wherein tube 14 moves into and out of the assembly, in assembly 80 tube 14 is substantially fixed, and does not move.

During both unrolling and rolling of bag 12, there is typically a delay in equalization of pressure within system 40, because of the length of tubes 14 and 34, as well as because the tubes are typically narrow. To allow for this delay, as well as for general safety concerns, assembly controller 62 is typically configured to halt operation of motor 50 if the pressure measured by sensor 60 reaches or exceeds a preset safety value, such as 1010 mbar. To prevent spasmodic operation of the motor, and consequent fitful rolling or unrolling of bag 12, controller 62 is also typically configured to provide a time delay before reactivating motor 50 once the motor has halted due the preset pressure safety value being reached.

Figure 4:
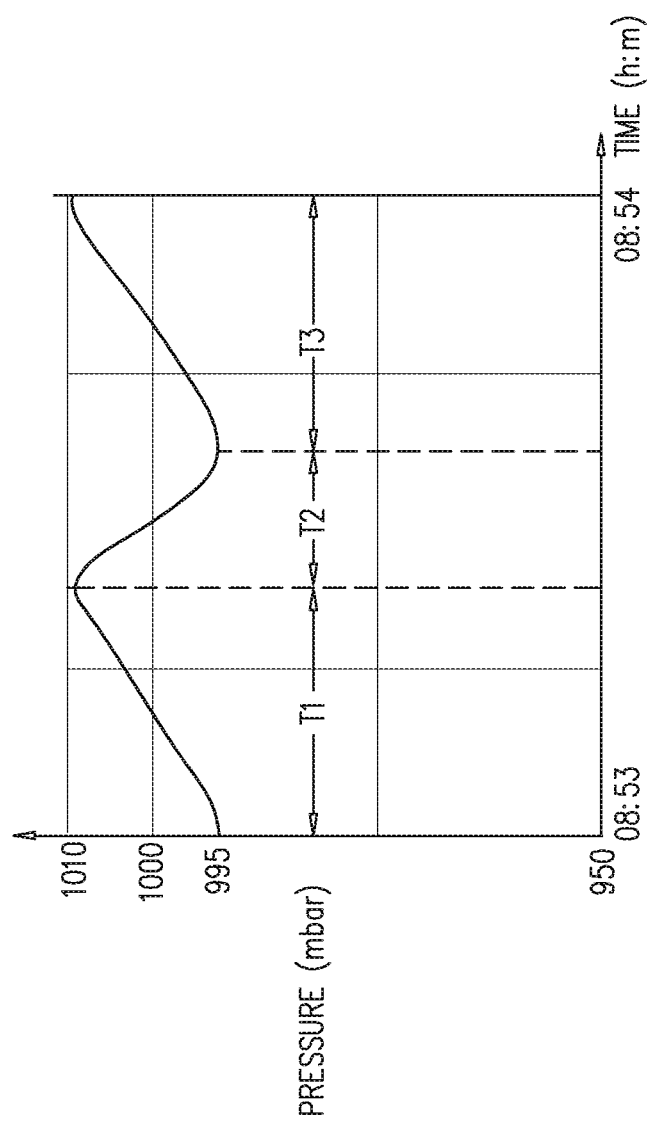
FIG. 4 is a schematic graph of pressure vs. time, according to an embodiment of the present invention.

FIG. 4 is a schematic graph of pressure vs. time, according to an embodiment of the present invention. The graph shows the change of pressure, as measured by sensor 60, as implantee 20 operates assembly 10 or assembly 80 to roll bag 12 onto spindle 56. Rolling the bag onto the spindle increases the pressure in system 40, and particularly initially in bag 12. Thus, during an initial period T1, the pressure measured by sensor 60 increases until it reads the preset safety value of 1010 mbars, at which point controller 62 deactivates motor 50, so that bag 12 does not roll onto (or roll off) spindle 56. During the preset delay time period, herein assumed to be period T2, the pressures in system 40 equalize, and during this time period motor 50 remains deactivated. At the conclusion of the preset delay time period, and assuming implantee 20 has operated assembly 10 or 80 to continue rolling bag 12 onto spindle 56, controller 62 reactivates motor 50 to further roll the bag onto the spindle, so that during a time period T3 the pressure measured by sensor 60 again increases until the pressure safety value is reached, whereupon the controller deactivates the motor.

Implantee 20 may operate assembly 10 or assembly 80 to unroll bag 12 from spindle 56, for example to alleviate the overpressure referred to above. In this case the unrolling by motor 50 is typically configured to be slow enough so that the pressure remains substantially equal throughout closed system 40.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
    an enclosure;
    a fluid-tight bag located within the enclosure;
    a fluid-tight valve connected to the fluid-tight bag;
    a tube, having a first end connected to the fluid-tight bag via the fluid-tight valve, and a second end connected to a balloon within a breast implant fitted to an implantee;
    a spindle, located within the enclosure, connected to the fluid-tight bag, and configured to rotate under control of the implantee so as to roll the fluid-tight bag onto the spindle or to unroll the fluid-tight bag from the spindle, and thus transfer a fluid, contained in the balloon, the tube, and the fluid-tight bag, therebetween;
    a motor, located within the enclosure, connected to the spindle so as to rotate the spindle; and
    tracks, located within the enclosure, along which the motor and the spindle are configured to slide while the spindle rotates.

2. The apparatus according to claim 1, and comprising a pressure sensor connected to the fluid-tight bag so as to measure pressure therein.

3. The apparatus according to claim 1, and comprising a controller within the enclosure configured to operate the spindle, and further comprising a further controller, located remote from the enclosure and under control of the implantee, configured to communicate wirelessly with the controller.

4. The apparatus according to claim 1, wherein the fluid comprises a liquid.

5. The apparatus according to claim 1, wherein the fluid comprises a gas.

6. A method, comprising:
    providing an enclosure;
    locating a fluid-tight bag within the enclosure;
    connecting a fluid-tight valve to the fluid-tight bag;
    connecting a first end of a tube to the fluid-tight bag via the fluid-tight valve, and a connecting a second end of the tube to a balloon within a breast implant fitted to an implantee;
    connecting a spindle, located within the enclosure, to the fluid-tight bag, and configuring the spindle to rotate under control of the implantee so as to roll the fluid-tight bag onto the spindle or to unroll the fluid-tight bag from the spindle, and thus transfer a fluid, contained in the balloon, the tube, and the fluid-tight bag, therebetween;
    connecting a motor, located within the enclosure, to the spindle so as to rotate the spindle; and
    providing tracks, located within the enclosure, along which the motor and the spindle are configured to slide while the spindle rotates.

7. The method according to claim 6, and comprising connecting a pressure sensor to the fluid-tight bag so as to measure pressure therein.

8. The method according to claim 6, and comprising operating the spindle with a controller within the enclosure, and further comprising locating a further controller, remote from the enclosure and under control of the implantee, that is configured to communicate wirelessly with the controller.

9. The method according to claim 6, wherein the fluid comprises a liquid.

10. The method according to claim 6, wherein the fluid comprises a gas.

* * * * *